(12) United States Patent
Bailey

(10) Patent No.: US 10,096,764 B2
(45) Date of Patent: Oct. 9, 2018

(54) APPLICATION OF PIEZO TECHNOLOGY TO CONVERT ALTERNATING CURRENT (AC) LINE POWER TO ISOLATED DIRECT CURRENT (DC) POWER IN HIGH EXTERNAL MAGNETIC FIELDS

(71) Applicant: KONINKLIJKE PHILIPS N.V., Eindhoven (NL)

(72) Inventor: Paul Wayne Bailey, North Reading, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 313 days.

(21) Appl. No.: 15/108,798

(22) PCT Filed: Jan. 6, 2015

(86) PCT No.: PCT/IB2015/050085
§ 371 (c)(1),
(2) Date: Jun. 29, 2016

(87) PCT Pub. No.: WO2015/101962
PCT Pub. Date: Jul. 9, 2015

(65) Prior Publication Data
US 2016/0329483 A1 Nov. 10, 2016

Related U.S. Application Data

(60) Provisional application No. 61/923,921, filed on Jan. 6, 2014.

(51) Int. Cl.
*G01V 3/00* (2006.01)
*H01L 41/107* (2006.01)
(Continued)

(52) U.S. Cl.
CPC ............ *H01L 41/107* (2013.01); *A61B 5/055* (2013.01); *G01R 33/3815* (2013.01); *H02M 1/32* (2013.01);
(Continued)

(58) Field of Classification Search
CPC ... H01L 41/107; G01R 33/3815; G01R 33/56; G01R 33/341; G01R 33/546; G01R 33/385; H02M 1/32; H02M 1/44
See application file for complete search history.

(56) References Cited

U.S. PATENT DOCUMENTS 2,830,274 A 4/1958 Rosen
5,969,954 A * 10/1999 Zaitsu ................. H02M 3/337
310/319

(Continued)

FOREIGN PATENT DOCUMENTS

CN 1710794 12/2005
DE 102008038989 10/2009
(Continued)

*Primary Examiner* — Tung X Nguyen
*Assistant Examiner* — Dominic Hawkins

(57) ABSTRACT

A system (10) and a method (200) supply power in high external magnetic fields. Alternating current (AC) line power is converted (202) to isolated power using one or more piezoelectric transformers (18). The flow of AC line power to the piezoelectric transformers (18) is regulated (204) to maintain the isolated power at a predetermined voltage.

10 Claims, 15 Drawing Sheets

(51) Int. Cl.
*A61B 5/055* (2006.01)
*H02M 1/32* (2007.01)
*H02M 1/44* (2007.01)
*H02M 3/335* (2006.01)
*H02M 7/04* (2006.01)
*G01R 33/3815* (2006.01)
*H02M 1/00* (2006.01)
*G01R 33/341* (2006.01)
*G01R 33/385* (2006.01)
*G01R 33/54* (2006.01)
*G01R 33/56* (2006.01)

(52) U.S. Cl.
CPC ......... *H02M 1/44* (2013.01); *H02M 3/33523* (2013.01); *H02M 3/33569* (2013.01); *H02M 7/04* (2013.01); *A61B 2560/0214* (2013.01); *G01R 33/341* (2013.01); *G01R 33/385* (2013.01); *G01R 33/546* (2013.01); *G01R 33/56* (2013.01); *H02M 2001/007* (2013.01); *H02M 2001/0058* (2013.01); *H02M 2001/327* (2013.01); *Y02B 70/1491* (2013.01)

(56) References Cited

U.S. PATENT DOCUMENTS

| | | | |
|---|---|---|---|
| 8,659,921 B2* | 2/2014 | Buchwald | H02M 3/33507 363/75 |
| 2005/0062433 A1* | 3/2005 | Ongaro | H05B 41/2822 315/209 PZ |
| 2005/0285476 A1* | 12/2005 | Chou | H01L 41/044 310/317 |
| 2009/0045755 A1* | 2/2009 | Cheng | H05B 41/282 315/219 |

FOREIGN PATENT DOCUMENTS

| | | |
|---|---|---|
| JP | 2000150190 | 5/2000 |
| JP | 2003348855 | 12/2003 |
| JP | 5357033 | 12/2013 |
| TW | 200913450 | 3/2013 |

* cited by examiner

APPLICATION OF PIEZO TECHNOLOGY TO CONVERT ALTERNATING CURRENT (AC) LINE POWER TO ISOLATED DIRECT CURRENT (DC) POWER IN HIGH EXTERNAL MAGNETIC FIELDS

CROSS REFERENCE TO RELATED APPLICATIONS

This application is the U.S. National Phase application under 35 U.S.C. § 371 of International Application No. PCT/IB2015/050085, filed Jan. 6, 2015, published as WO 2015/101962 on Jul. 9, 2015, which claims the benefit of U.S. Provisional Patent Application Number 61/923,921 filed Jan. 6, 2014. These applications are hereby incorporated by reference herein.

The present application relates generally to power supplies. It finds particular application in conjunction alternating current (AC)/direct current (DC) power adapters for medical devices used in high external magnetic fields, and will be described with particular reference thereto. However, it is to be understood that it also finds application in other usage scenarios, and is not necessarily limited to the aforementioned application.

Traditional methods of converting AC line power to isolated DC power involve the use of ferrous, electromagnetic transformers and inductors. When an AC/DC power adapter employing such methods is used in high external magnetic fields, such as in the magnet room of a magnetic resonance imaging (MRI) facility, the power adapter must usually be positioned and mechanically secured at a safe distance from the magnet. Without securing the power adapter at a safe distance, the electromagnetic transformer and inductors can saturate from the high external magnetic field. This can cause the power adapter to lose its ability to convert power, overheat, or be damaged. Further, electromagnetic transformers have a significant magnetic attraction and without securing the power adapter at a safe distance, the power adapter can create a safety hazard by becoming a projectile.

A challenge with securing the power adapter away from the magnet is that often times a device powered by the power adapter needs to be used in close proximity to the magnet. Typically, this challenge is addressed by providing power via a long cable extending from the power adapter to the device, or by providing power from batteries local to the device and merely using the power adapter to charge the batteries. However, employing a long cable reduces portability and can pose a safety risk to both the device and users of the device since the users can trip over the cable. Further, batteries are limited in the amount of power that can be provided and have a useful life much shorter than the device itself.

Other less common methods of converting AC line power to isolated DC power involve the use of piezoelectric transformers, as described in U.S. Pat. No. 2,830,274 to Rosen et al. The piezoelectric methods are commonly used in AC/DC power adapters used to develop high AC voltages required for florescent backlight tubes used in displays, such as laptop displays. Further, the piezoelectric methods are commonly used in micro power energy harvesting to power remote sensors. More recently, the piezoelectric methods have been deployed in low power AC/DC adapters for notebook computers due to reduced size and weight. Challenges with power adapters employing the piezoelectric methods are that these adapters fail to provide sufficient power for medical applications. Further, such power adapters fail to generate an isolated low voltage DC output sufficient for medical applications and are only available for a single AC line voltage, most typically the relatively low AC line voltage of the United Sates.

The present application provides a new and improved system and method which overcome these problems and others.

In accordance with one aspect, a power supply for supplying power in high external magnetic fields is provided. The power supply includes one or more piezoelectric transformers converting alternating current (AC) line power to isolated power. The power supply further includes one or more regulator modules at least one of regulating the flow of AC line power to the piezoelectric transformers and regulating the flow of isolated power from the piezoelectric transformers to maintain a constant output voltage regardless of the AC line power.

In accordance with another aspect, a method for supplying power in high external magnetic fields. The method includes converting alternating current (AC) line power to isolated power using one or more piezoelectric transformers. The method further includes regulating the flow of AC line power to the piezoelectric transformers to maintain the isolated power at a predetermined voltage.

In accordance with another aspect, a power supply for supplying power in high external magnetic fields is provided. The power supply includes a piezoelectric core converter module configured for converting alternating current (AC) line power to isolated power using one or more piezoelectric transformers. The power supply further includes a regulator module configured for regulating the flow of AC line power to the piezoelectric core converter module to maintain the isolated power at a predetermined voltage.

One advantage resides in eliminating magnetic immunity issues.

Another advantage resides in eliminating projectile risks.

Another advantage resides in an alternating current (AC)/direct current (DC) power adapter integral with the device being powered.

Another advantage resides in support for the wide range of worldwide AC line voltages and frequencies.

Another advantage resides in closer positioning to a magnet producing high external magnetic fields.

Another advantage resides in improved portability.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The present application provides an improved approach for converting alternating current (AC) line power to medically isolated direct current (DC) power useful for powering medical devices without the use of electromagnetic components, such as electromagnetic transformers and inductors. Instead of using electromagnetic components for power conversion, the improved approach employs one or more piezoelectric transformers. By eliminating electromagnetic components, the improved approach can achieve isolated power conversion that is immune to high magnetic fields, such as those generated by the main magnetic of a magnetic resonance imaging (MRI) system.

To provide a DC output at increased power and voltage levels, such as those useful for many medical devices needed in proximity to the main magnetic of a MRI system, the number of piezoelectric transformers can be increased. Even more, to allow power conversion operation over the full range of worldwide AC line voltages and frequencies, conversion using the piezoelectric transformers can be regulated by, for example, a microcontroller.

Figure 1:
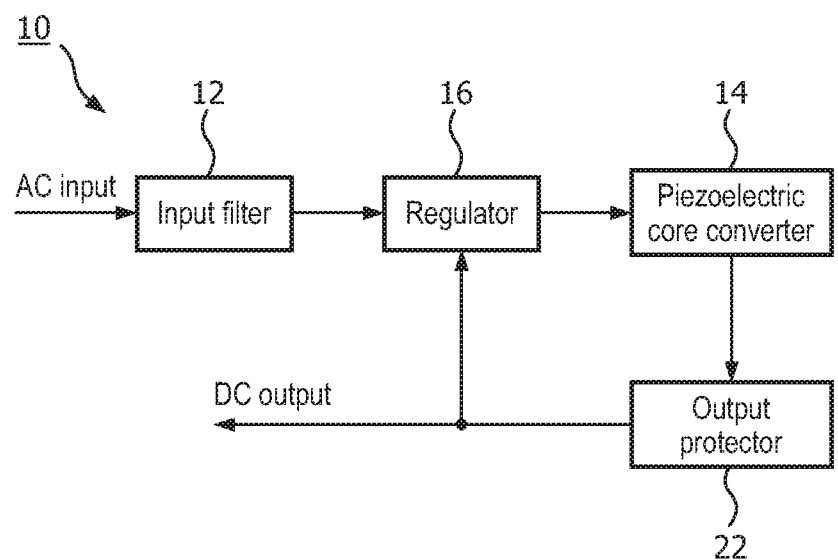
FIG. 1 illustrates a power adapter employing one or more piezoelectric transformers and a feedback loop for regulating the output of the power adapter.

With reference to FIG. 1, an AC/DC power adapter 10 for use in high external magnetic fields is provided. As used herein, a high external magnetic field is a magnetic field above 2000 gauss (G). An input filter module 12 receives AC power from an external source, such as a power grid or generator, over an AC power line and filters the received AC power. The input filter module 12 filters the received AC power to remove noise, such as radio frequency interference. Additionally, or alternatively, the input filter 12 filters the received AC power to protect the power adapter 10 from power surges, brown outs, and other atypical conditions associated with the AC power line. The voltage and the frequency of the AC power line can span the full range of worldwide AC line voltages and frequencies. For example, the voltage of the AC power line can range from 90-250 volts (V), and the frequency of the AC power line can range from 50-60 hertz (Hz).

The filtered power passes from the input filter module 12 to a piezoelectric core converter module 14 through a regulator module 16, which regulates the flow of filtered power to the piezoelectric core converter module 14. The piezoelectric core converter module 14 employs one or more piezoelectric transformers 18 (see FIG. 4C) to convert the regulated, filtered power from the regulator module 16 to an isolated DC power output. A piezoelectric transformer converts input electrical energy to mechanical energy and then converts that mechanical energy back to output electrical energy that is galvanically and therefore safely isolated from the input electrical energy. To increase the power and voltage levels of the DC power output, the number of piezoelectric transformers can be increased and arranged in parallel.

The regulator module 16 regulates the flow of filtered power to the piezoelectric core converter module 14 to maintain the DC power output at a constant, predetermined voltage, regardless of the voltage and the frequency of the AC power line, using feedback from the DC power output. The regulator module 16 can further regulate the flow of filtered power to protect the piezoelectric transformers 18 from overheating, power spikes and brown outs on the AC power line, and overloading. Suitably, a microcontroller 20 (see FIG. 4D) of the regulator module 16 manages the regulation of the filtered power.

The DC power output from the piezoelectric core converter module 14 is passed to an external load through an output protector module 22. The external load can, for example, be a medical device. Examples of medical devices include patient monitors, displays, entertainment devices, infusion pumps, injectors, motors, anesthesia workstations, cameras, battery chargers, and communication devices. The output protector module 22 ensures that the voltage and/or current of the DC power output do not exceed predefined limits. This advantageously protects both the power adapter 10 and the external load.

Those skilled in the art should appreciate that even though the input filter module 12 and the output protector module 22 were illustrated and described in connection with FIG. 1, those modules 12, 22 are not required for proper operation of the power adapter 10. Hence, in some instances, the power adapter 10 is without the input filter module 12 and/or the output protector module 22.

Figure 2:
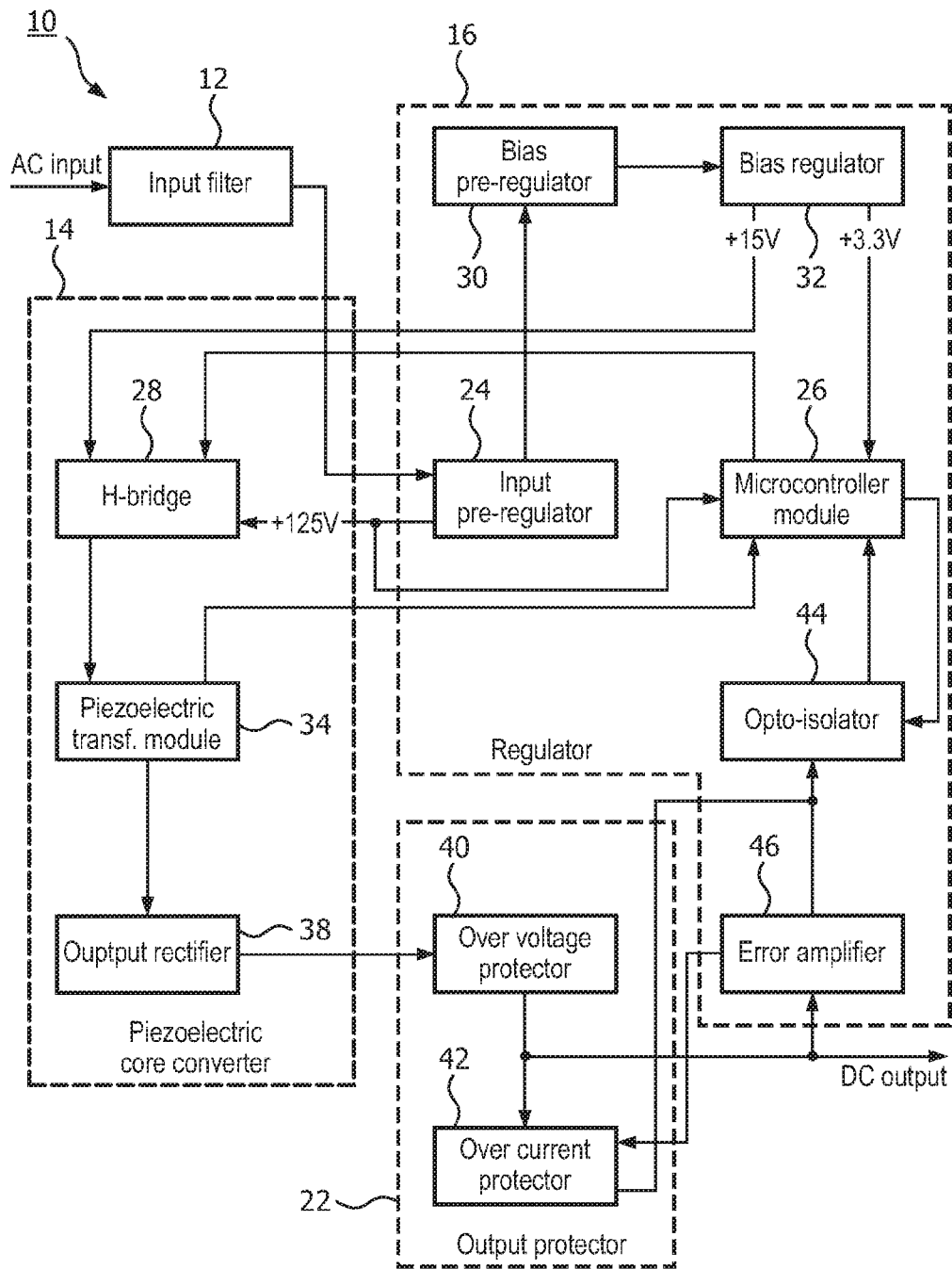
FIG. 2 illustrates a more specific embodiment of the power adapter of FIG. 1.

With reference to FIG. 2, a more specific embodiment of the power adapter 10 described in FIG. 1 is provided. The correspondences with the modules 12, 14, 16, 22 of FIG. 1 are shown in dash boxes. As above, the input filter module 12 receives AC power from the external source. The filtered power is provided to an input pre-regulator module 24, which converts the filtered power to a regulated, DC power output. The input pre-regulator module 24 suitably converts the filtered power to the regulated, DC power output by rectifying the filtered power. Therefore, the voltage of the regulated, DC power output is typically dependent upon the received AC power. In the United States of America, for example, the regulated, DC power output is about 125 volts (V). The regulated, DC power out is provided to a microcontroller module 26 and an H-bridge module 28. The input pre-regulator module 24 further provides filtered power to a bias pre-regulator module 30, which prepares the filtered power for use by a bias regulator module 32.

The bias regulator module 32 receives prepared, filtered power from the bias pre-regulator module 30 and converts the power to a first regulated, DC power output and a second regulated, DC power outputs. The first regulated, DC power output has a voltage sufficient to power the microcontroller module 26, such as 3.3V, and the second regulated, DC power output has a voltage sufficient to power the H-bridge module 28, such as 15V. In some instances, the first and the second regulated, DC power outputs can be one and the same depending upon the power requirements of the H-bridge module 28 and the microcontroller module 26.

The H-bridge module 28 receives the second regulated, DC power output from the bias regulator module 32, which is used to power the H-bridge module 28. Further, the H-bridge module 28 receives the regulated, DC power output from the input pre-regulator module 24 and generates a high frequency pulse train from the regulated, DC power output of the input pre-regulator module 24. The high frequency pulse train is duty cycle controlled in accordance with a control signal from the microcontroller module 26 to generate a constant root mean square (RMS) voltage. This advantageously removes the large variations in voltages from worldwide AC line power. The high frequency pulse train is provided to a piezoelectric transformer module 34.

The piezoelectric transformer module 34 includes an air core inductor 36 (see FIG. 4C) receiving the high frequency pulse train. The air core inductor 36 resonates with the input capacitance of one or more piezoelectric transformers 18 (see FIG. 4C) of the piezoelectric transformer module 34, thus generating a sinusoidal input to the piezoelectric transformers 18 at a frequency just above the mechanical resonance of the piezoelectric transformers 18. An air core inductor advantageously avoids saturation of the inductor in the presence of high magnetic fields. Further, the sine wave of the sinusoidal input minimizes other harmonics that create heat in the piezoelectric transformers 18 without contributing to power conversion. Even more, the sine wave of the sinusoidal input also helps to significantly reduce radiated emissions, which can create image artifacts in an MRI, and to reduce the dv/dt stress on the piezoelectric transformers 18.

The piezoelectric transformers 18 convert the electrical energy of the sinusoidal input to mechanical vibrations, which are in turn converted to electrical energy in the form of an isolated, lower voltage sinusoid at the output of the piezoelectric transformers 18. The output sinusoid is rectified by an output rectifier module 38 to form a DC power output that is safely isolated from the AC power line. The isolated DC power output then passes through an over voltage protector module 40 and an over current protector module 42 to ensure the voltage and current of the DC power output stay within predefined limits.

Figure 3:
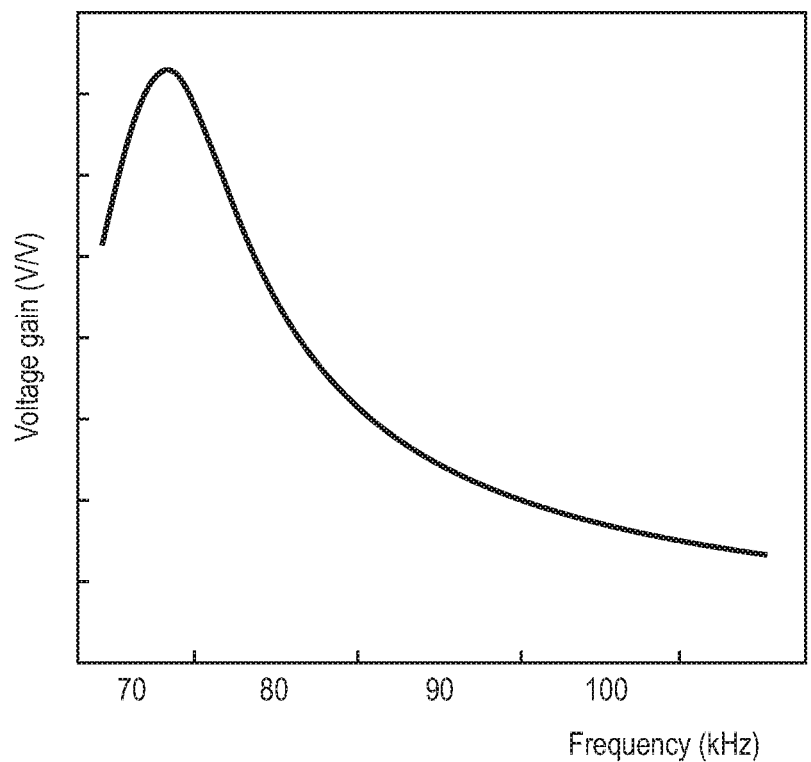
FIG. 3 illustrates a graph of voltage gain of a piezoelectric transformer as a function of frequency.

The microcontroller module 26 receives the first regulated, DC power output from the bias regulator module 32, which is used to power the microcontroller module 26. A microcontroller 20 (see FIG. 4D) of the microcontroller module 26 monitors the isolated DC power output via an opto-isolator module 44. In that regard, an error amplifier module 46 determines the difference between the isolated DC power output and the expected DC power output. The difference is then provided to the microcontroller 20 through the opto-isolator module 44. Based on the difference signal, the microcontroller 20 adjusts the frequency of the pulse train in order to regulate the voltage of the DC power output to a constant DC voltage regardless of output load variations. This pulse frequency regulation makes use of the voltage gain properties of the piezoelectric transformers 18. FIG. 3 illustrates a graph of voltage gain of a piezoelectric transformer (output voltage/input voltage) as a function of frequency (kilohertz (kHz)).

The microcontroller 20 can further monitor the temperature of the piezoelectric transformers 18 using a signal indicator of temperature received from the piezoelectric transformer module 34 and/or a signal indicative of the voltage of the AC power line received from the input pre-regulator module 24. Based on the temperature signal and/or the power line signal, the microcontroller 20 can take action to protect the piezoelectric transformers 18 from AC line brown outs or surges, output overloads, overheating, and so on by, for example, disabling the external load.

Figure 4A:
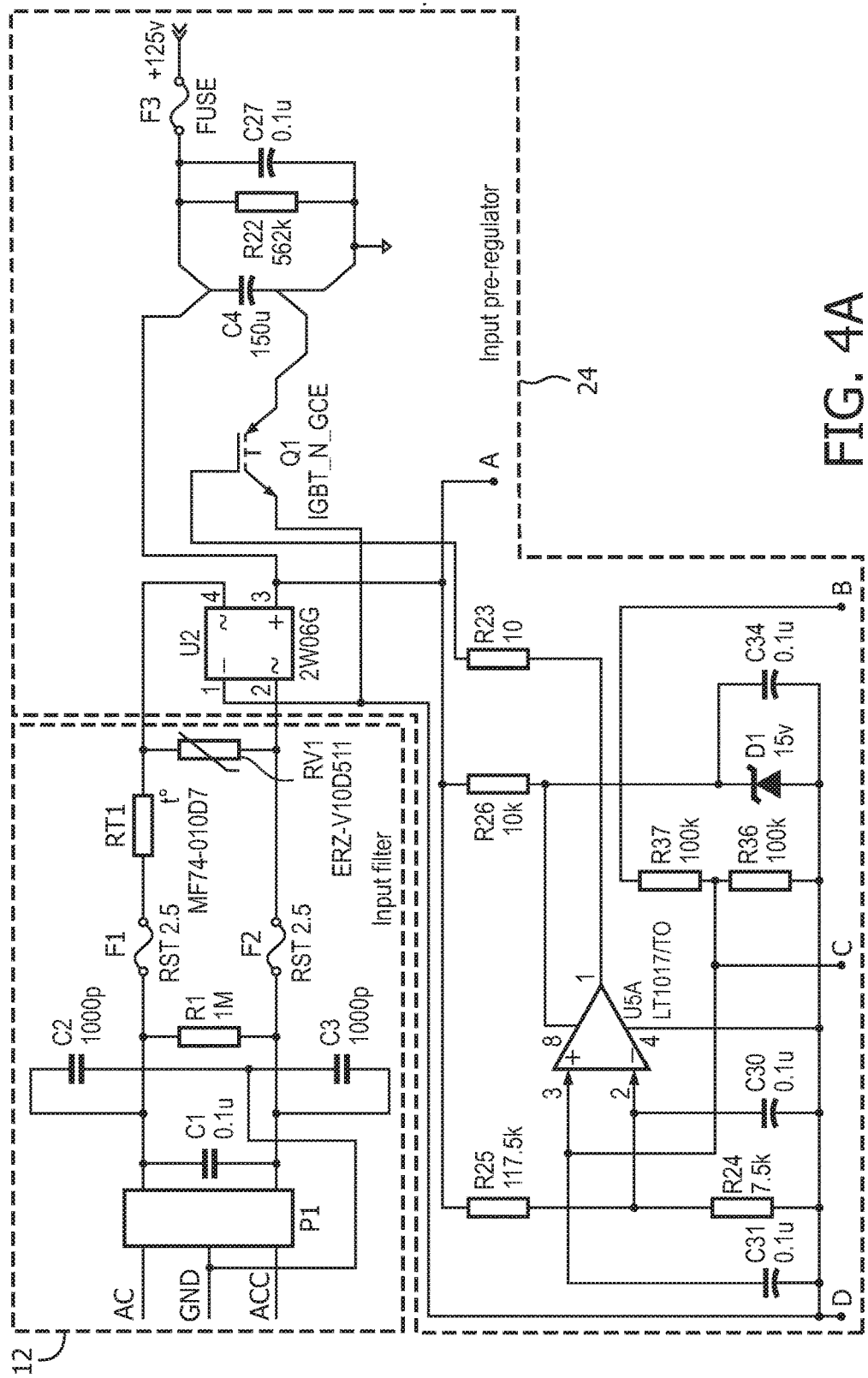
FIG. 4A illustrates circuits for the input filter and the input pre-regulator modules of FIG. 2.
Figure 4B:
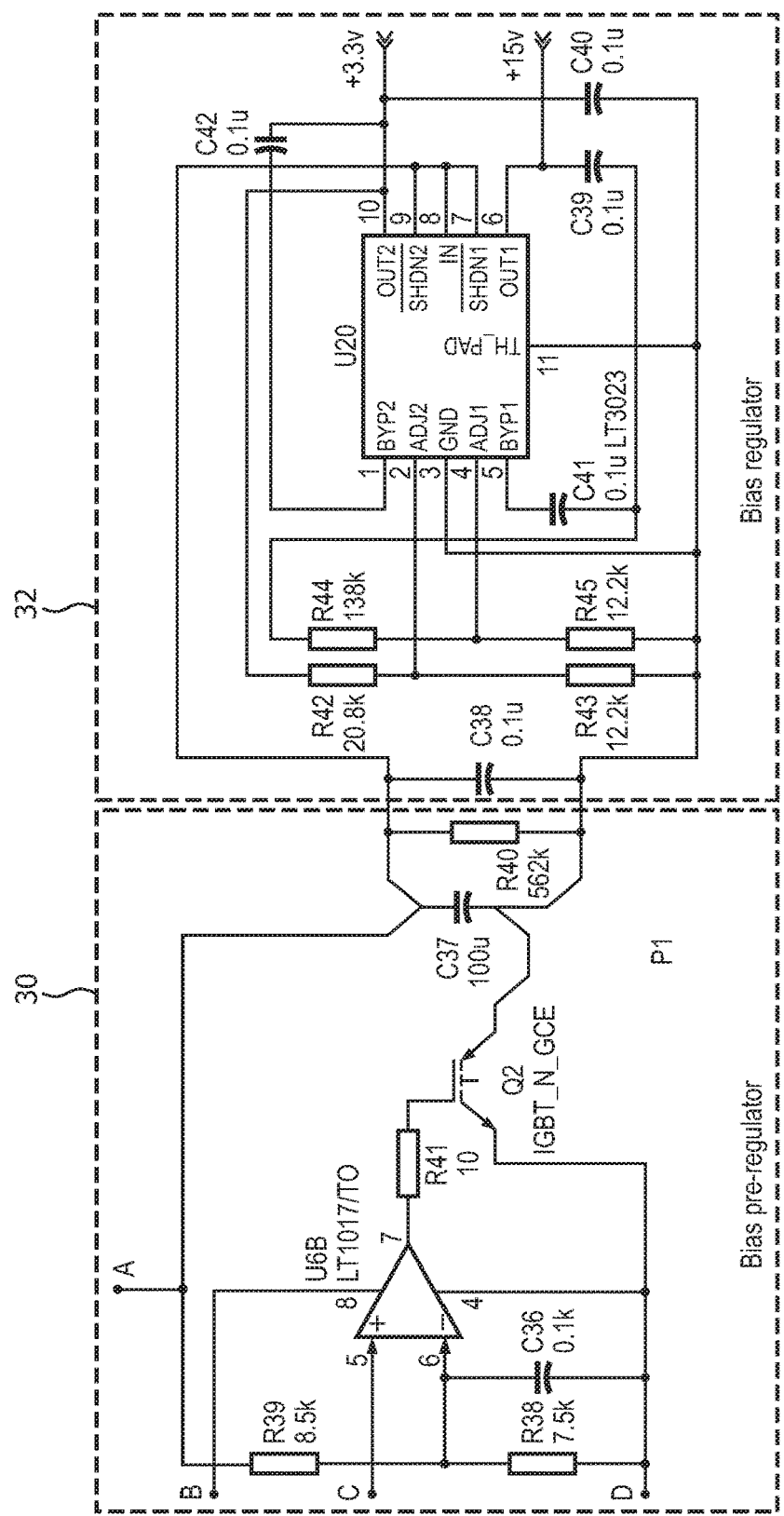
FIG. 4B illustrates circuits for the bias pre-regulator and the bias regulator modules of FIG. 2.
Figure 4C:
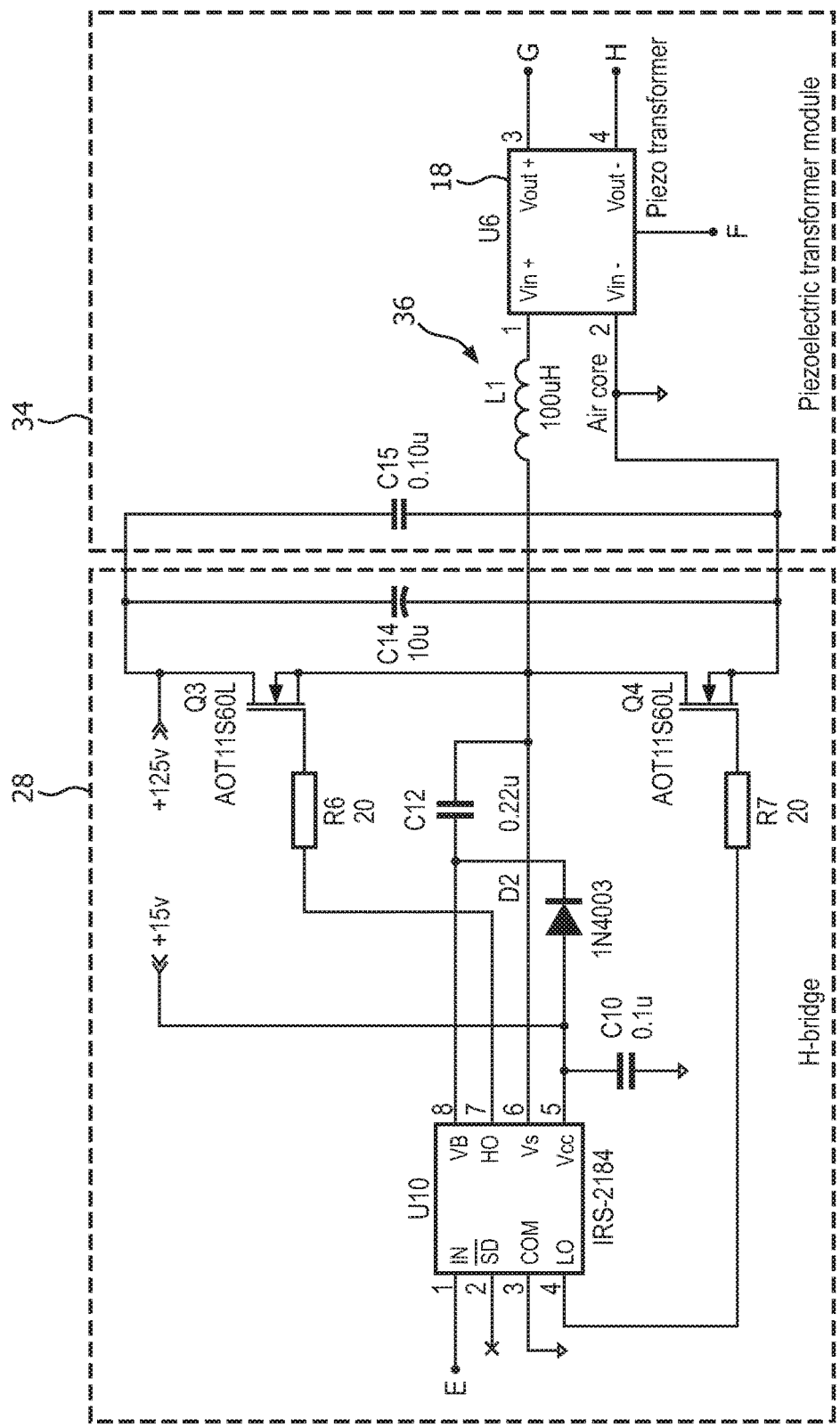
FIG. 4C illustrates circuits for the H-bridge and the piezoelectric transformer modules of FIG. 2.
Figure 4D:
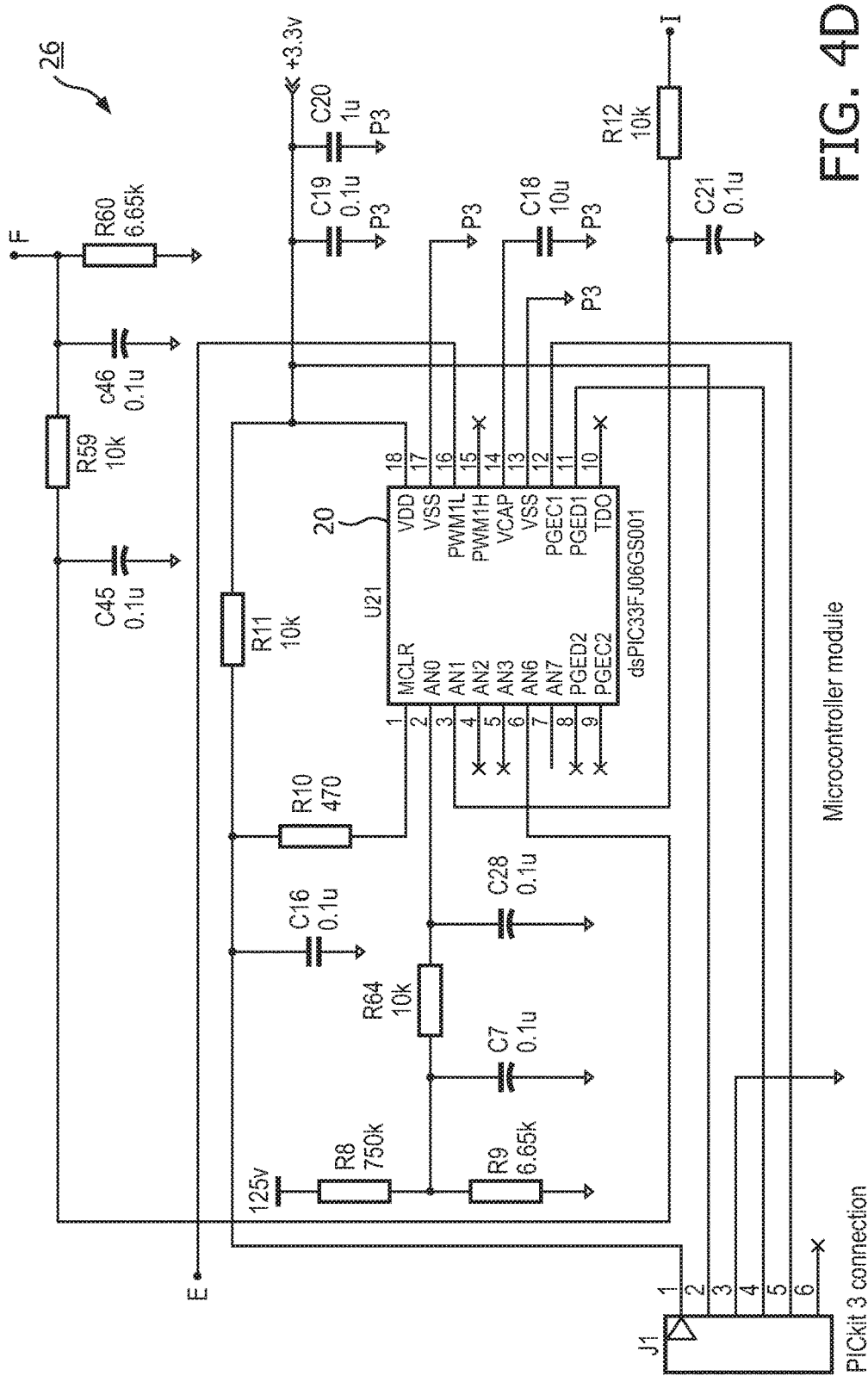
FIG. 4D illustrates circuits for the microcontroller module of FIG. 2.
Figure 4E:
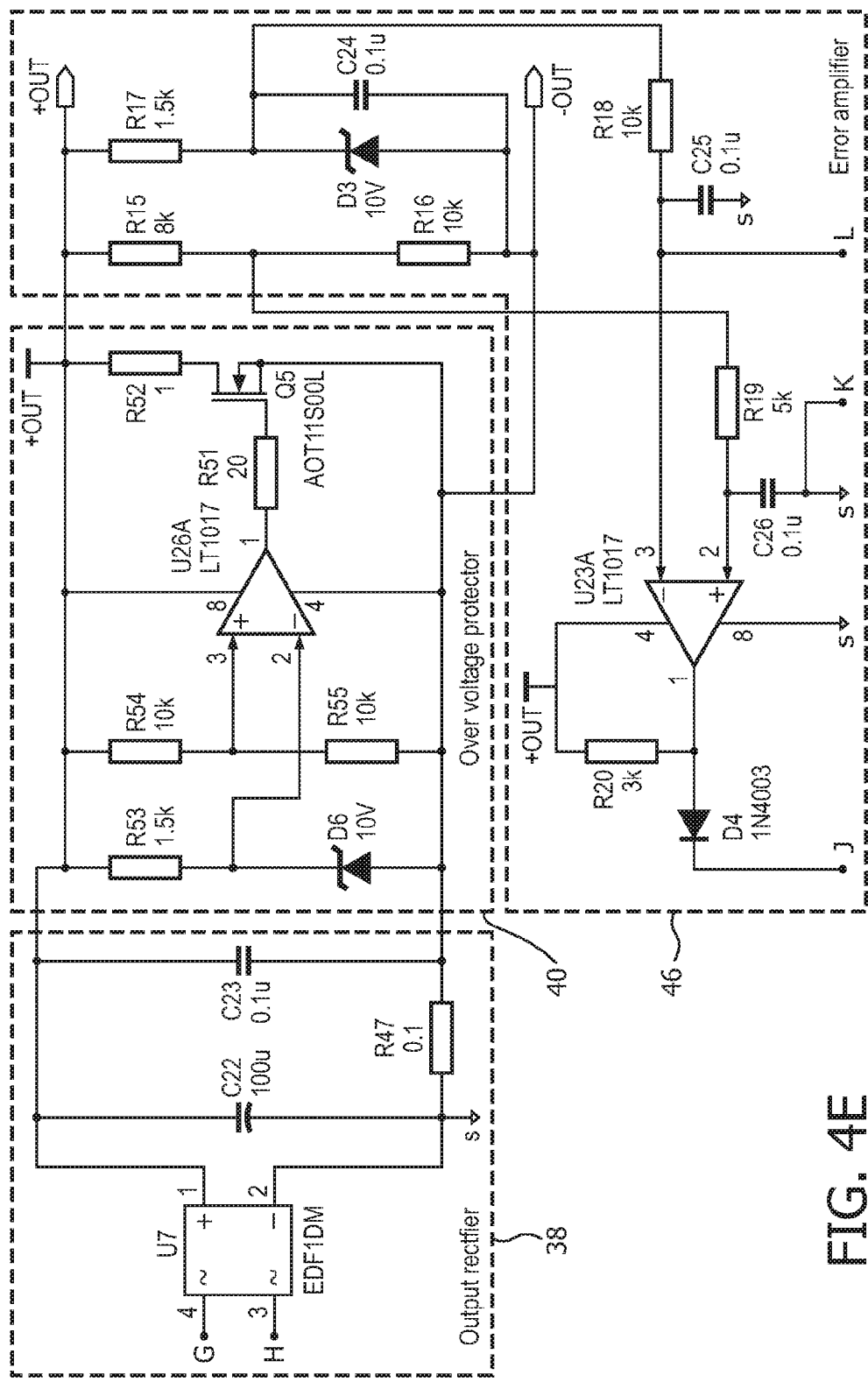
FIG. 4E illustrates circuits for the output rectifier, the over voltage protector, and the error amplifier modules of FIG. 2.
Figure 4F:
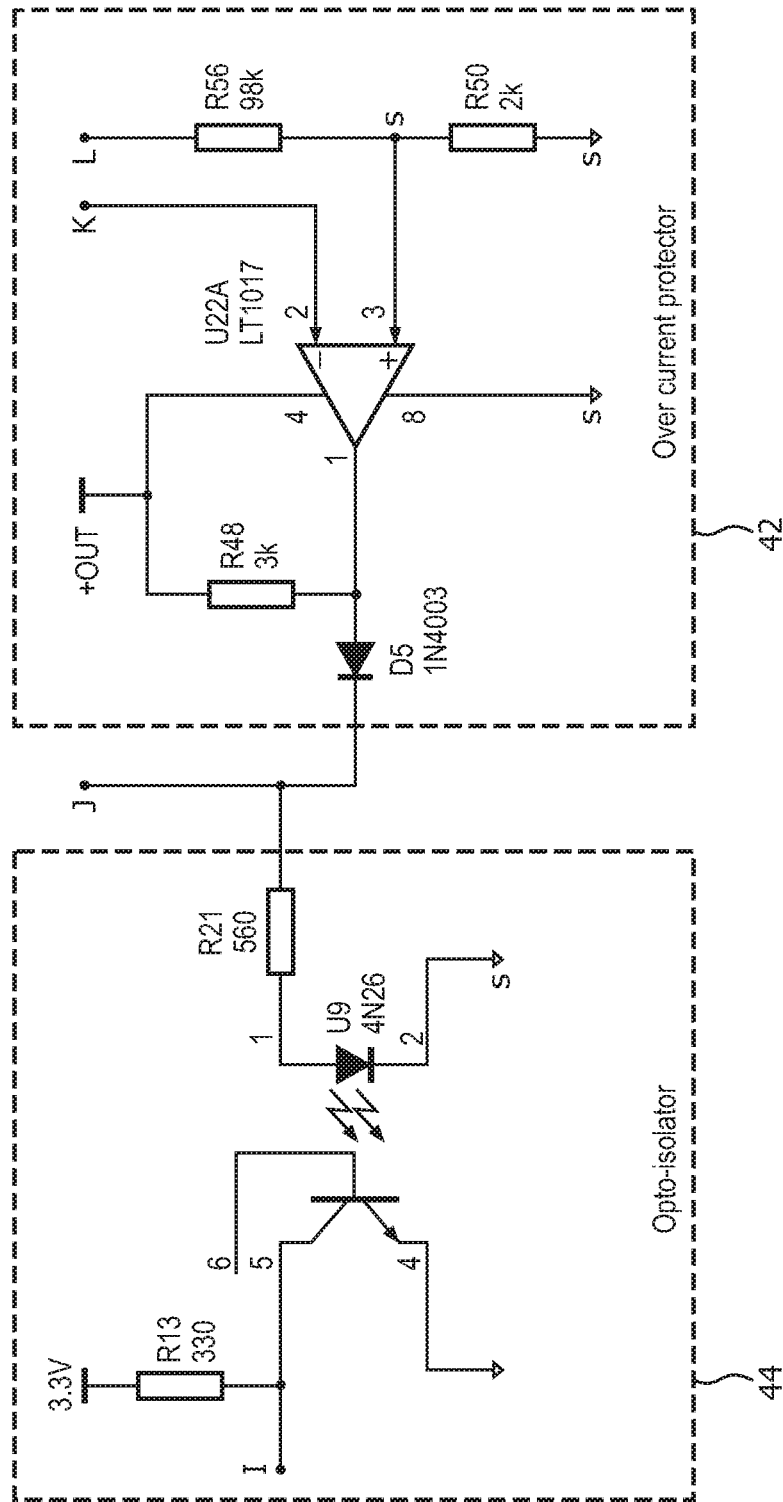
FIG. 4F illustrates circuits for the opto-isolator and the over current protector modules of FIG. 2.

With reference to FIGS. 4A-4F, a more specific embodiment of the power adapter 10 described in FIG. 2 is provided. The correspondences with the modules 12, 24-34, 38-46 of FIG. 2 are shown in dashed boxes. As seen, each of the modules 12, 24-34, 38-46 corresponds to an electrical circuit. FIG. 4A illustrates a circuit for the input filter module 12, and a circuit for the input pre-regulator module 24. FIG. 4B illustrates a circuit for the bias pre-regulator module 30, and a circuit for the bias regulator module 32. FIG. 4C illustrates a circuit for the H-bridge module 28, and a circuit for the piezoelectric transformer module 34. The circuit for the piezoelectric transformer module 34 illustrates the interconnection of the air inductor 36 and the piezoelectric transformers 18. FIG. 4D illustrates a circuit for the microcontroller module 26, the circuit including the microcontroller 20. FIG. 4E illustrates a circuit for the output rectifier module 38, a circuit for the over voltage protector module 40, and a circuit for the error amplifier module. FIG. 4F illustrates a circuit for the opto-isolator module 44, and a circuit for the over current protector module 42.

The embodiment of the power adapter 10 described in FIGS. 4A-F was experimentally tested in both at 1.5 Tesla (T) and a 3.0T MRI environment. During testing, it was found that the power adapter 10 was capable of operating in magnetic fields of at least 3T and with an output power in excess of 50 watts (W). Even more, it was found that the power adapter 10 did not cause any image artifacts to appear on 1.5T MRIs or 3T MRIs. Moreover, the power adapter 10 had negligible magnetic pull in the presence of a 3T MRI magnet. The power adapter 10 was able to sit unassisted in the bore of the 3T magnet. Further, no effects on the operation of the power adapter 10 from the magnetic field were observed in any orientation. The power adapter 10 operated successfully all the way into the bore of the 3T magnet.

Figure 5:
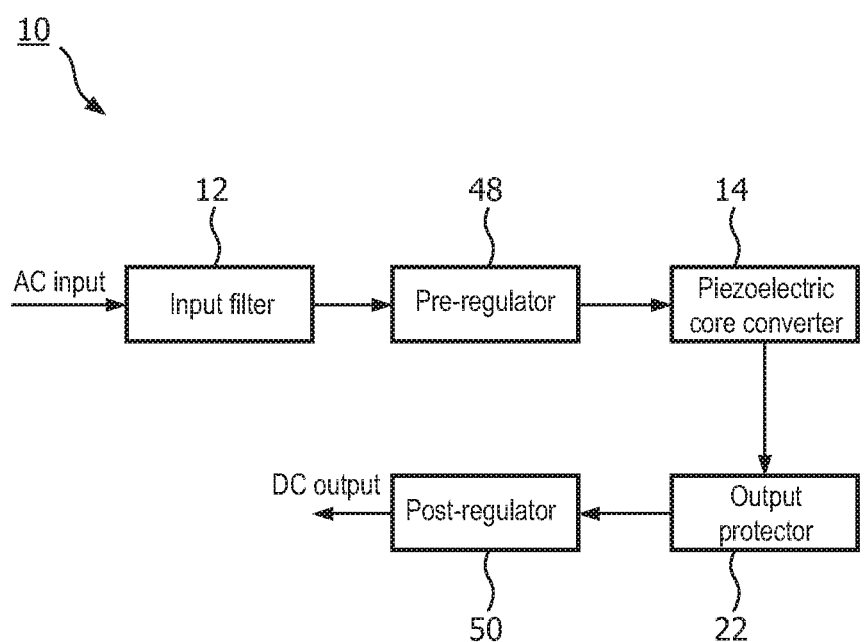
FIG. 5 illustrates an alternative embodiment of the power adapter of FIG. 1 without the feedback loop for regulating the output of the power adapter.

With reference to FIG. 5, an alternative embodiment of the AC/DC power adapter 10 described in FIG. 1 is illustrated. The input filter module 12 and the output protector module 22 remain as described above. Similarly, the piezoelectric core converter module 14 remains as described above except that it outputs an isolated AC power output. However, in contrast to having a single regulator module 30 with feedback, as described in connection with FIG. 1, this embodiment of the power adapter 10 includes a pre-regulator module 48 and a post-regulator module 50.

The pre-regulator module 48 regulates the flow of filtered power to the piezoelectric core converter module 14 to maintain the frequency and voltage of the filtered power provided to the piezoelectric core converter module 14 at predetermined levels, regardless of the voltage and the frequency of the AC power line. Suitably, the filtered power provided to the piezoelectric core converter is sinusoidal with a frequency just above the mechanical resonance of the piezoelectric transformers 18. The post-regulator module 50 regulates the flow of isolated AC power from the piezoelectric core converter module 14 and converts the isolated AC power to an isolated DC power output. In that regard, the post-regulator module 50 maintain the DC power output at a constant, predetermined voltage, regardless of the voltage of the isolated AC power output by the piezoelectric core converter module 14.

Figure 6A:
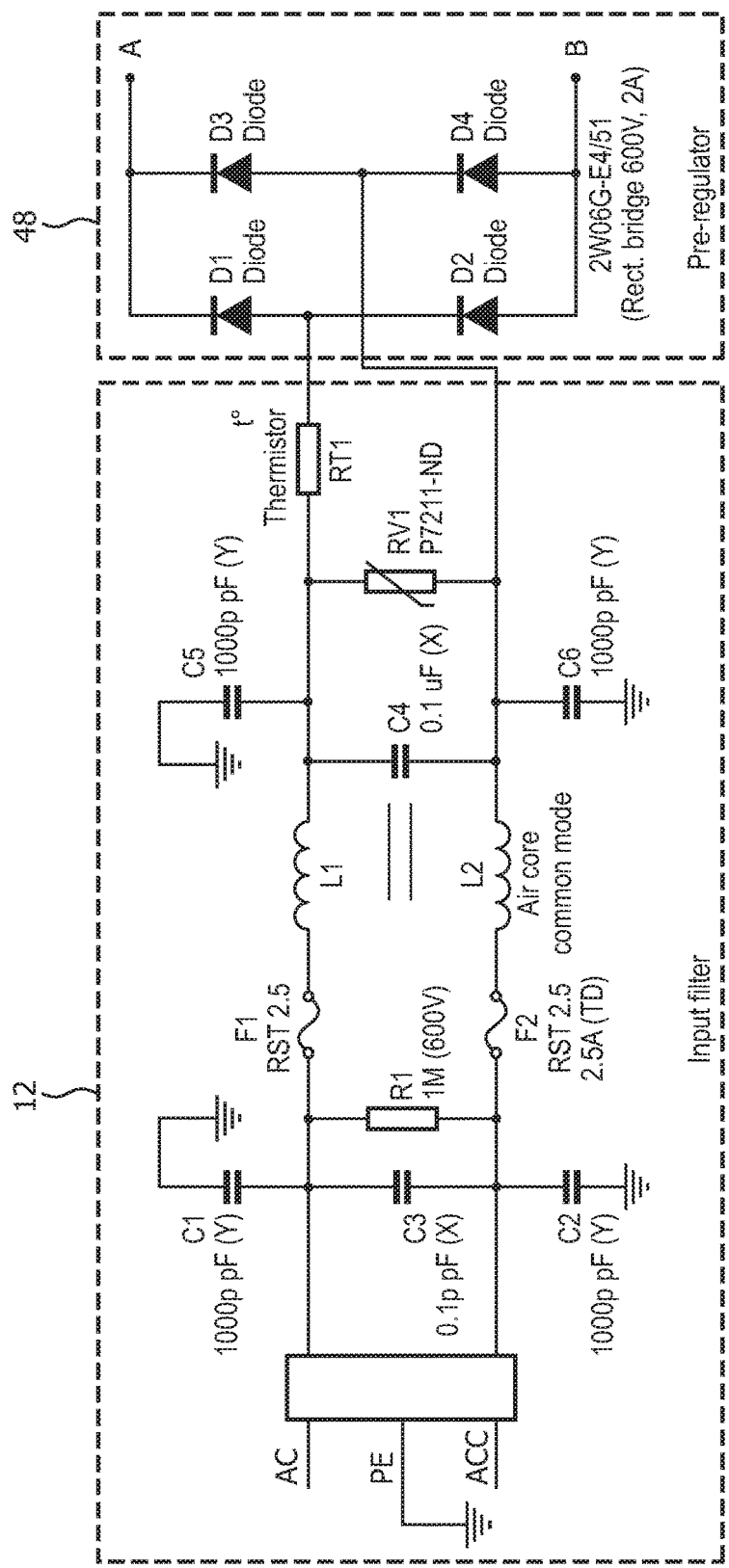
FIG. 6A illustrates a circuit for the input filter module and a part of a circuit for the pre-regulation module of FIG. 5.
Figure 6B:
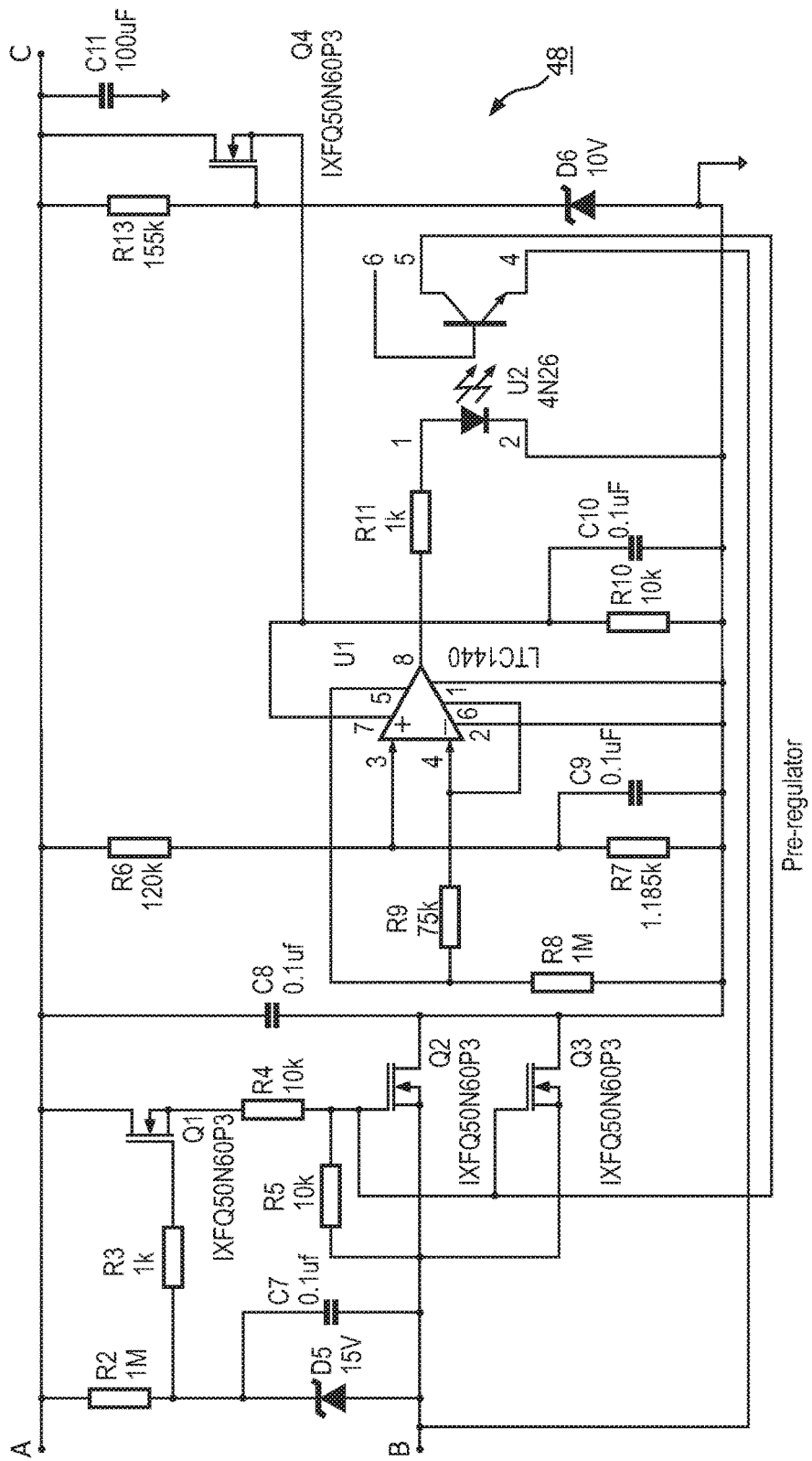
FIG. 6B illustrates a part of a circuit for the pre-regulation module of FIG. 5.
Figure 6C:
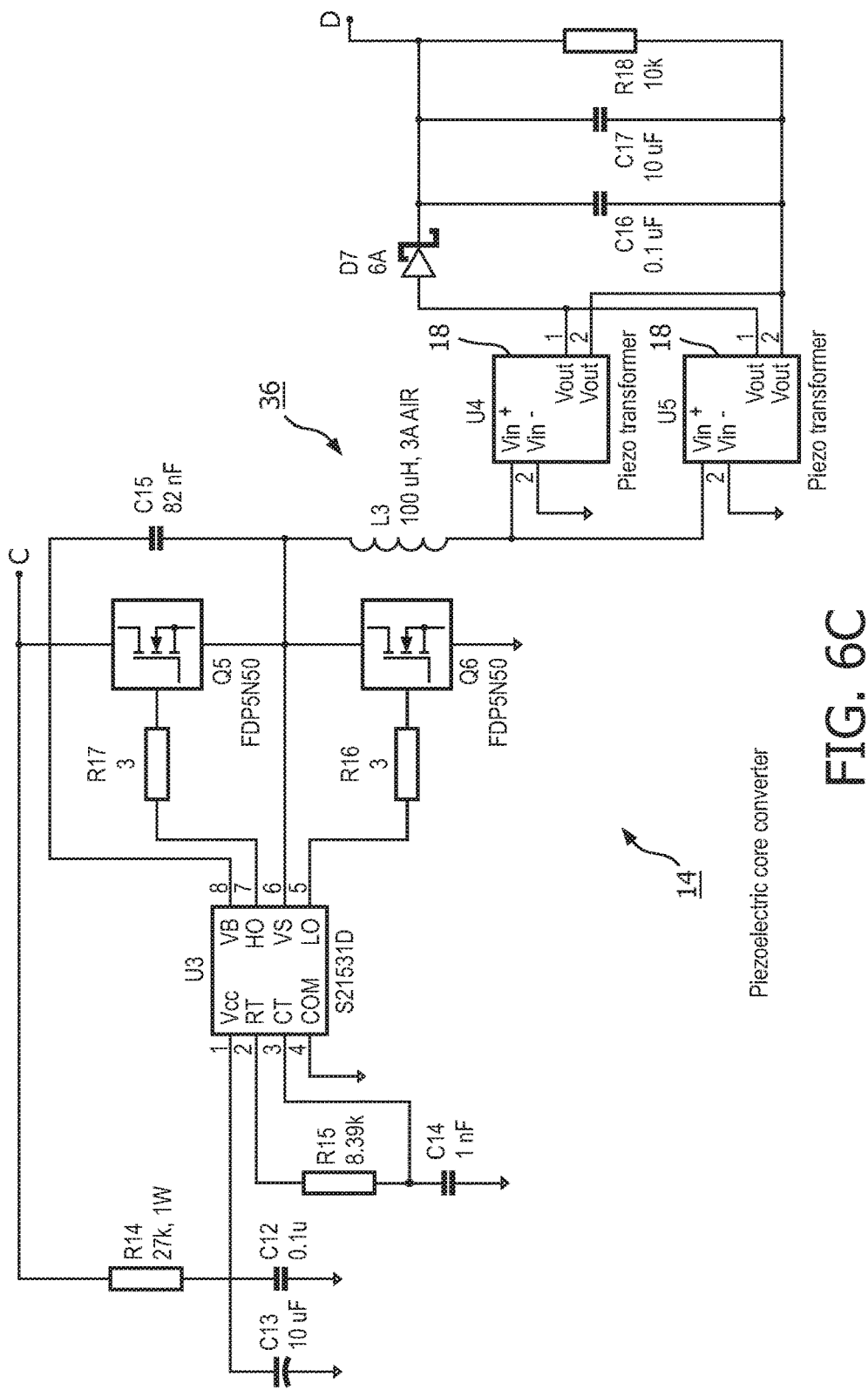
FIG. 6C illustrates a circuit for the piezoelectric core converter module of FIG. 5.
Figure 6D:
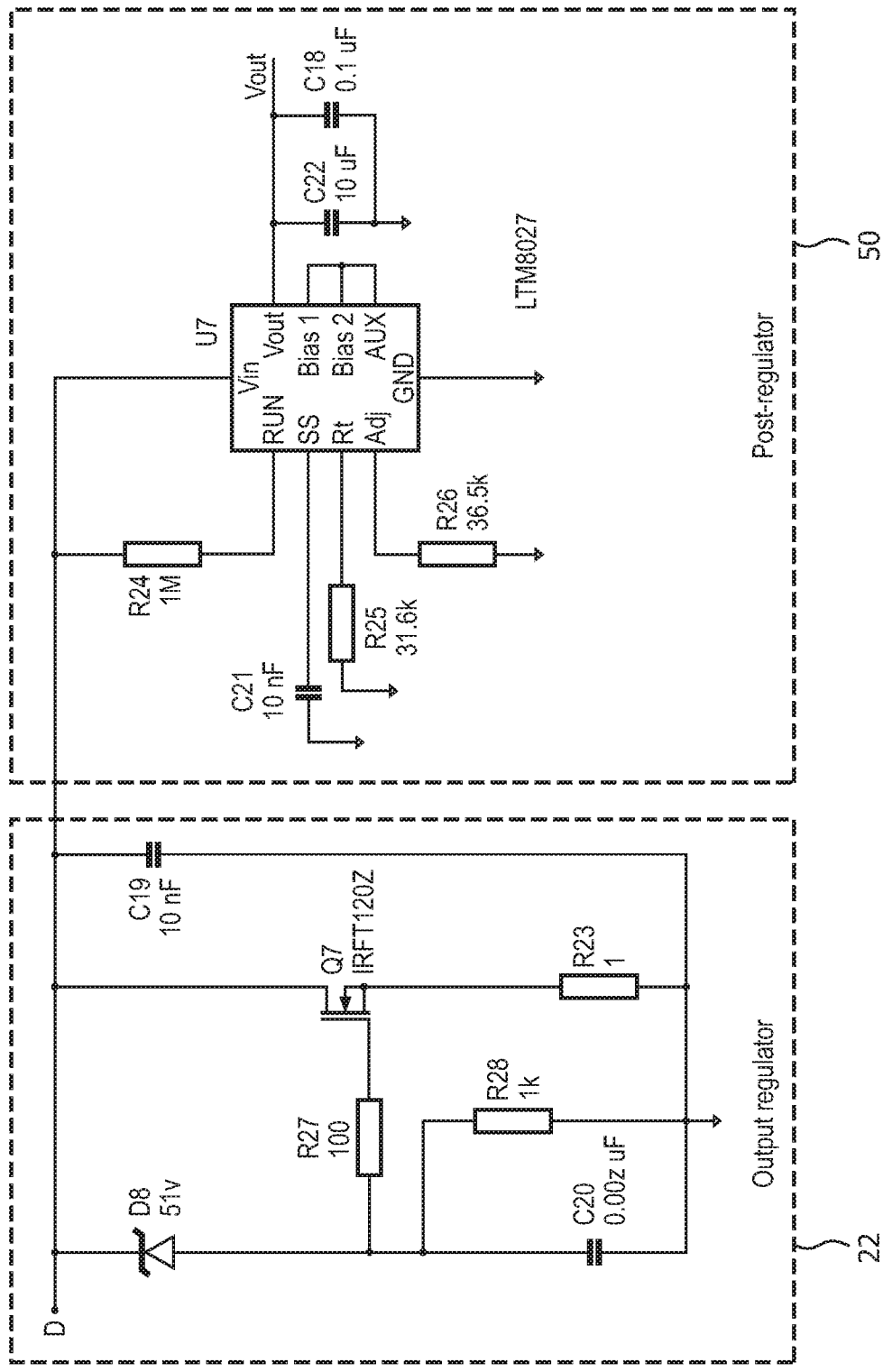
FIG. 6D illustrates circuits for the output protector and the post regulator modules of FIG. 5.

With reference to FIGS. 6A-4D, a more specific embodiment of the power adapter 10 described in FIG. 5 is provided. The correspondences with the modules 12, 14, 22, 48, 50 of FIG. 5 are shown in dashed boxes. As seen, each of the modules 12, 14, 22, 48, 50 corresponds to an electrical circuit. FIG. 6A illustrates a circuit for the input filter module 12, and a part of a circuit for the pre-regulation module 48. FIG. 6B illustrates a part of a circuit for the pre-regulation module 48. FIG. 6C illustrates a circuit for the piezoelectric core converter module 14. The circuit for the piezoelectric core converter module 14 illustrates the interconnection of the air inductor 36 and the piezoelectric transformers 18. Further, the circuit for the piezoelectric core converter module 14 illustrates the parallel connection of multiple piezoelectric transformers 18 to increase the power output of the power adapter 10. FIG. 6D illustrates a circuit for the output protector module 22, and a circuit for the post regulator module 50.

Figure 7:
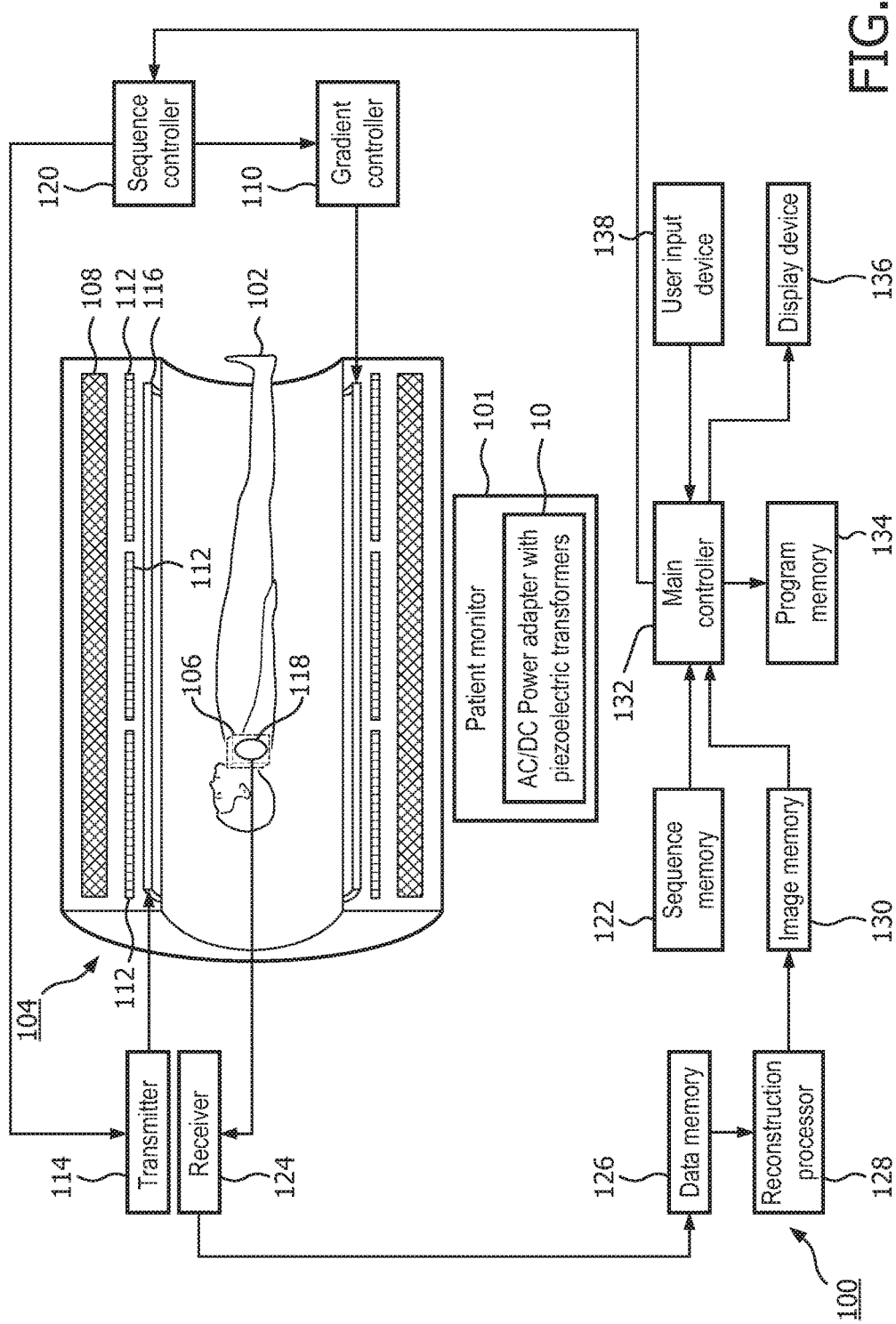
FIG. 7 illustrates a magnetic resonance imaging (MRI) system with a power adapter employing one or more piezoelectric transformers positioned proximate a main magnet.

With reference to FIG. 7, an MRI system 100 within which a device 101 employing the power adapter 10 can be employed is provided. The device 101 is suitably a medical device, such as the illustrated patient monitor. The MRI system 100 uses magnetic resonance (MR) to generate one or more diagnostic images of a target volume of a patient 102. The system 100 includes a scanner 104 defining an imaging (or scan) volume 106 sized to accommodate the target volume. A patient support can be employed to support the patient 102 and to position the target volume near the isocenter of the imaging volume 106.

The scanner 104 includes a main magnet 108 that creates a strong, static $B_0$ magnetic field extending through the imaging volume 106. The main magnet 108 typically employs superconducting coils to create the static $B_0$ magnetic field. However, the main magnet 108 can also employ permanent or resistive magnets. Insofar as superconducting coils are employed, the main magnet 108 includes a cooling system, such as a liquid helium cooled cryostat, for the superconducting coils. The strength of the static $B_0$ magnetic field is commonly one of 0.23T, 0.5T, 1.5T, 3T, 7T, and so on in the imaging volume 106, but other strengths are contemplated.

A gradient controller 110 of the scanner 104 is controlled to superimpose magnetic field gradients, such as x, y and z gradients, on the static $B_0$ magnetic field in the imaging volume 106 using a plurality of magnetic field gradient coils 112 of the scanner 104. The magnetic field gradients spatially encode magnetic spins within the imaging volume 106. Typically, the plurality of magnetic field gradient coils 112 include three separate magnetic field gradient coils spatially encoding in three orthogonal spatial directions.

Further, one or more transmitters 114, such as a transceiver, are controlled to transmit $B_1$ resonance excitation and manipulation radiofrequency (RF) pulses into the imaging volume 106 with one or more transmit coil arrays, such as a whole body coil 116 and/or a surface coil 118, of the scanner 104. The $B_1$ pulses are typically of short duration and, when taken together with the magnetic field gradients, achieve a selected manipulation of magnetic resonance. For example, the $B_1$ pulses excite the hydrogen dipoles to resonance and the magnetic field gradients encode spatial information in the frequency and phase of the resonance signal. By adjusting the RF frequencies, resonance can be excited in other dipoles, such as phosphorous, which tend to concentrate in known tissues, such as bones.

A sequence controller 120 controls the gradient controller 110 and/or the transmitters 114 according to imaging sequences to produce spatially encoded MR signals within the imaging volume 106. An imaging sequence defines a sequence of $B_1$ pulses and/or magnetic field gradients. Further, the imaging sequences can be received from a device or system being remote or local to the sequence controller, such as a sequence memory 122.

One or more receivers 124, such as a transceiver, receive the spatially encoded magnetic resonance signals from the imaging volume 106 and demodulate the received spatially encoded magnetic resonance signals to MR data sets. The MR data sets include, for example, k-space data trajectories. To receive the spatially encoded magnetic resonance signals, the receivers 124 use one or more receive coil arrays, such as the whole body coil 116 and/or the surface coil 118, of the scanner 104. The receivers 124 typically store the MR data sets in a data memory 126.

A reconstruction processor 128 reconstructs the MR data sets into MR images or maps of the imaging volume 106. This includes, for each MR signal captured by the MR data sets, spatially decoding the spatial encoding by the magnetic field gradients to ascertain a property of the MR signal from each spatial region, such as a pixel or voxel. The intensity or magnitude of the MR signal is commonly ascertained, but other properties related to phase, relaxation time, magnetization transfer, and the like can also be ascertained. The MR images or maps are typically stored in an image memory 130.

A main controller 132 controls the reconstruction processor 128 and the sequence controller 120 to generate one or more diagnostic images of the target volume using one or more scans of the target volume. For each scan, the target vessel is positioned within the imaging volume 106. For example, the patient 102 is positioned on the patient support. The surface coil 118 is then positioned on the patient 102 and the patient support moves the target volume into the imaging volume 106. The size of the imaging volume 106 can vary between scans.

Once the target volume is positioned within the imaging volume 106, the main controller 132 controls the sequence controller 120 according to scan parameters, such as number of slices, and provides the sequence controller 120 with an imaging sequence. The imaging sequence can, for example, be stored in the sequence memory 122. As noted above, an imaging sequence defines a sequence of $B_1$ pulses and/or magnetic field gradients that produce spatially encoded MR signals from the imaging volume 106. Further, the main controller 132 can control the receivers 124 according to scan parameters. For example, the main controller 132 can adjust the gain of the receivers 124.

The main controller 132 can carry out the foregoing functionality by software, hardware or both. Where the main controller 132 employs software, the main controller 132 includes at least one processor executing the software. The software is suitably stored on a program memory 134, which can be local or remote from the main controller 42. Further, the main controller 132 can be managed by a user using a graphical user interface presented to the user by way of a display device 136 and a user input device 138. The user can, for example, initiate imaging, display images, manipulate images, etc.

Notwithstanding that the reconstruction processor 128 and the sequence controller 120 were illustrated as external to the main controller 132, it is to be appreciated that one or both of these components can be integrated with the main controller 132 as software, hardware or a combination of both. For example, the reconstruction processor 128 can be integrated with the main controller 132 as a software module executing on the at least one processor of the main controller 132.

Figure 8:
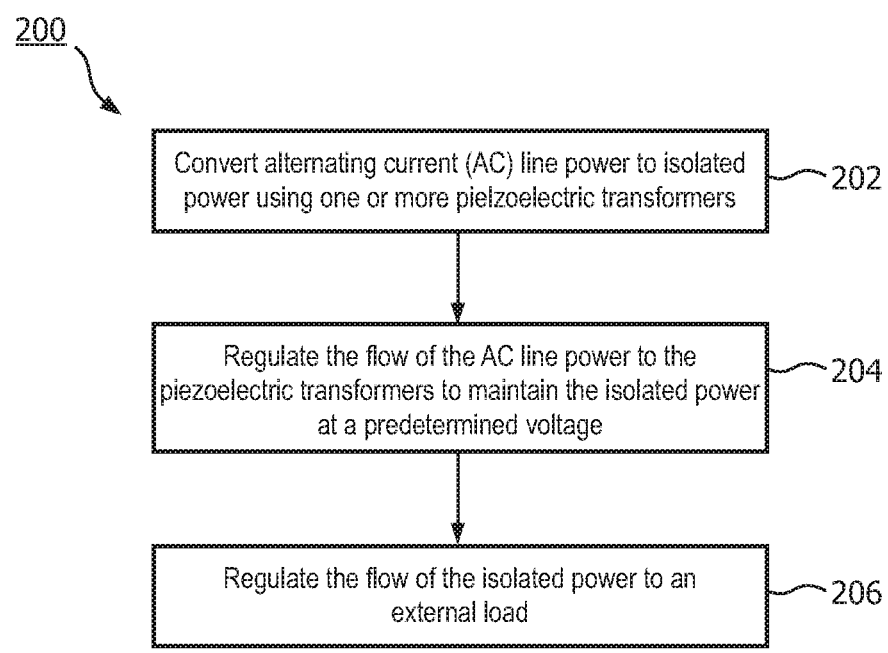
FIG. 8 illustrates a method for supplying power in high external magnetic fields using piezoelectric transformers.

With reference to FIG. 8, a method 200 for supplying power in external magnetic fields according to the above discussion is provided. The method 200 is performed by a power supply, such as the AC/DC power adapter 10, in a high external magnetic field. A high external magnetic field is typically a magnetic field greater than 2000 G. Such magnetic fields are common proximate (e.g., within a few feet) of a main magnetic 108 of a magnetic resonance imaging MRI system 100.

The method 200 includes converting 202 alternating current AC line power to isolated power using one or more piezoelectric transformers 18. This is carried out by the piezoelectric core converter module 14. The isolated power can be DC or AC (compare FIG. 1 and FIG. 5). When the isolated power is DC power, it is typically provided to an external load 101 without further conversion and/or regulation. Otherwise, additional conversion and/or regulation are often needed for the external load 101. The converting typically includes generating a sinusoidal input to the piezoelectric transformers 18 at a frequency above the mechanical resonance of the piezoelectric transformers 18 by an air core inductor 36.

The flow of AC line power to the piezoelectric transformers 18 is regulated 204 to maintain the isolated power at a predetermined voltage (RMS voltage when the isolated power is AC). This is carried out by the regulator module 16 or the pre-regulator module 48 depending upon the number of regulation stages. The regulating can include receiving measurements of the isolated power and regulating the flow of AC line power to piezoelectric transformers 18 based on the received measurements. Further, the regulating can include converting the AC line power to a pulse train and controlling a duty cycle of the pulse train to maintain the isolated power at the predetermined voltage. Even more, the regulating can include monitoring the temperature of the piezoelectric transformers 18 and/or monitoring the AC line power. Based on the monitoring, the piezoelectric transformers 18 can be protected from damage by, for example, disconnecting external loads and/or the power line power from the piezoelectric transformers 18.

In some instances, as described in FIG. 5, the flow of the isolated power to an external load 101 can be regulated 206 after the conversion. This is carried out by the post-regulator module 50. Typically, the post-regulation includes converting the isolated power, which is typically AC, to isolated DC power sufficient for powering the external load 101. Regardless of the voltage of the isolated power, the isolated DC power remains constant. Hence, in embodiments including post-regulation, there are two stages of regulation: a pre-regulation stage and a post-regulation stage.

As used herein, a memory includes any device or system storing data, such as a random access memory (RAM) or a read-only memory (ROM). Further, as used herein, a processor includes any device or system processing input device to produce output data, such as a microprocessor, a microcontroller, a graphic processing unit (GPU), an application-specific integrated circuit (ASIC), an FPGA, and the like; a controller includes any device or system controlling another device or system; a user input device includes any device, such as a mouse or keyboard, allowing a user of the user input device to provide input to another device or system; and a display device includes any device for displaying data, such as a liquid crystal display (LCD) or a light emitting diode (LED) display.

The invention has been described with reference to the preferred embodiments. Modifications and alterations may occur to others upon reading and understanding the preceding detailed description. For example, while the foregoing discussion focused on an AC/DC power adapter, those skilled in the art will appreciate that the piezoelectric transformers can be applied to other types of power supplies. It is intended that the invention be construed as including all such modifications and alterations insofar as they come within the scope of the appended claims or the equivalents thereof.

The invention claimed is:

1. A power supply for supplying power in high external magnetic fields, the power supply comprising:
    a piezoelectric core converter module configured for converting alternating current (AC) line power to isolated direct current (DC) power using one or more piezoelectric transformers; and
    a regulator module configured for regulating the flow of AC line power to the piezoelectric core converter module to maintain the isolated power at a predetermined voltage;
    wherein the regulator module includes a microcontroller module and a bias regulator module which provides a first regulated DC power sufficient to power the microprocessor module and a second regulated DC power;
    wherein the piezoelectric core converter module includes an H-bridge module which receives the second regulated DC power from the bias regulator and generates a high frequency pulse train;
    wherein a module determines a difference between the isolated DC power and an expected isolated DC power and the microcontroller controls the H-bridge module to adjust a duty cycle of the high frequency pulse train.

2. The power supply according to claim 1, wherein the piezoelectric core converter module includes an air core inductor configured for generating from high frequency pulse train a sinusoidal input to the piezoelectric transformers at a frequency above the mechanical resonance of the piezoelectric transformers.

3. The power supply according to claim 1, wherein the one or more piezoelectric transformers includes a plurality of piezoelectric transformers connected in parallel to increase power output of the power supply.

4. The power supply according to claim 1, wherein the regulator module is further configured for:
    monitoring the temperature of the piezoelectric transformers and/or monitoring the AC line power; and
    protecting the piezoelectric transformers from damage based on the monitoring.

5. The power supply according to claim 1, wherein the high magnetic field is greater than 2000 gauss (G).

6. A medical system comprising:
    a magnetic resonance imaging (MRI) scanner including a main magnetic which generates a high external magnetic field; and
    the power supply according to claim 1 positioned proximate to the main magnetic and providing power to an external load.

7. A method for supplying power in high external magnetic fields, the method comprising:
    converting alternating current (AC) line power to isolated direct current (DC) power using one or more piezoelectric transformers; and
    regulating the flow of AC line power to the piezoelectric transformers to maintain the isolated power at a predetermined voltage;
    wherein the regulating includes providing a first regulated DC power; sufficient to power a microprocessor module and a second regulated DC power;
    wherein the converting includes receiving the second regulated DC power and generating a high frequency pulse train;

wherein a difference between the isolated DC power and expected isolated DC power is determined and used by the microcontroller to adjust a duty cycle of the high frequency pulse train.

8. The method according to claim 7, wherein the converting includes:
   generating a sinusoidal input to the piezoelectric transformers at a frequency above the mechanical resonance of the piezoelectric transformers by an air core inductor.

9. The method according to claim 7, wherein the regulating includes:
   monitoring the temperature of the piezoelectric transformers and/or monitoring the AC line power; and
   protecting the piezoelectric transformers from damage based on the monitoring.

10. The method according to claim 7, further including:
    positioning the piezoelectric transformers proximate a main magnetic of a magnetic resonance imaging (MRI) system, the main magnet generating the high external magnetic fields.

\* \* \* \* \*